United States Patent
Holmberg et al.

[11] Patent Number: 6,019,790
[45] Date of Patent: Feb. 1, 2000

[54] HEART VALVE HOLDER HAVING A LOCKING COLLAR

[75] Inventors: William R. Holmberg; Juan Carlos Ordonez, both of St. Paul, Minn.; Mary T. Draney, Palo Alto, Calif.; Thomas F. Hinnenkamp, White Bear Lake, Minn.

[73] Assignee: St. Jude Medical, Inc., St. Paul, Minn.

[21] Appl. No.: 08/962,756

[22] Filed: Nov. 3, 1997

Related U.S. Application Data

[63] Continuation of application No. 08/730,867, Oct. 18, 1996, abandoned, and a continuation-in-part of application No. 08/962,752, Nov. 3, 1997, and a continuation of application No. 08/719,192, Sep. 24, 1996, abandoned, which is a continuation-in-part of application No. 08/449,145, May 24, 1995, Pat. No. 5,578,076.

[51] Int. Cl.$^7$ ........................................................ A61F 2/24
[52] U.S. Cl. ................................................ 623/2; 606/99
[58] Field of Search .......................... 623/2, 900; 606/99

[56] References Cited

U.S. PATENT DOCUMENTS

| | | | |
|---|---|---|---|
| 3,828,787 | 8/1974 | Anderson et al. | 128/303 R |
| 3,860,005 | 1/1975 | Anderson et al. | 128/303 R |
| 4,655,218 | 4/1987 | Kulik et al. | 128/321 |
| 4,679,556 | 7/1987 | Lubock et al. | 128/303 R |
| 4,683,883 | 8/1987 | Martin | 128/303 R |
| 4,755,181 | 7/1988 | Igoe | 623/2 |
| 4,865,600 | 9/1989 | Carpentier et al. | 623/2 |
| 4,932,965 | 6/1990 | Phillips | 623/2 |
| 5,041,130 | 8/1991 | Cosgrove et al. | 623/2 |
| 5,236,450 | 8/1993 | Scott | 623/2 |
| 5,350,420 | 9/1994 | Cosgrove et al. | 623/2 |
| 5,370,685 | 12/1994 | Stevens | 623/2 |
| 5,403,305 | 4/1995 | Sauter et al. | 606/1 |
| 5,443,502 | 8/1995 | Caudillo et al. | 623/2 |
| 5,476,510 | 12/1995 | Eberhardt et al. | 623/2 |
| 5,480,425 | 1/1996 | Ogilive | 623/2 |
| 5,578,076 | 11/1996 | Krueger et al. | 623/2 |
| 5,735,894 | 4/1998 | Krueger et al. | 623/2 |
| 5,824,068 | 10/1998 | Bugge | 623/2 |

FOREIGN PATENT DOCUMENTS

| | | | |
|---|---|---|---|
| 1008937 | 7/1984 | U.S.S.R. | |
| 1690738 | 4/1989 | U.S.S.R. | |
| 1690739 | 11/1991 | U.S.S.R. | 623/2 |
| 9117720 | 11/1991 | WIPO | |
| 9418881 | 9/1994 | WIPO | |
| 9517139 | 6/1995 | WIPO | |
| WO 95/15715 | 6/1995 | WIPO | |

*Primary Examiner*—Bruce E. Snow
*Attorney, Agent, or Firm*—Hallie A. Finucane, Esq.; Westman, Champlin & Kelly, P.A.

[57] ABSTRACT

A prosthetic heart valve holder includes a set of jaws. Each jaw includes a distal end adapted for coupling to the prosthetic heart valve and a proximal end. A hinge assembly pivotally couples the jaws together between the distal and proximal ends. The hinge assembly allows movement of the jaws between an engaged position for grasping the prosthetic heart valve and an disengaged position in which the prosthetic heart valve is free from the distal ends. A locking collar is attached to the jaws and is movable between a first position in which the proximal ends are free from the collar, and a second position in which the collar holds the proximal ends of the jaws whereby the distal ends are held in position to engage the prosthetic heart valve.

25 Claims, 20 Drawing Sheets

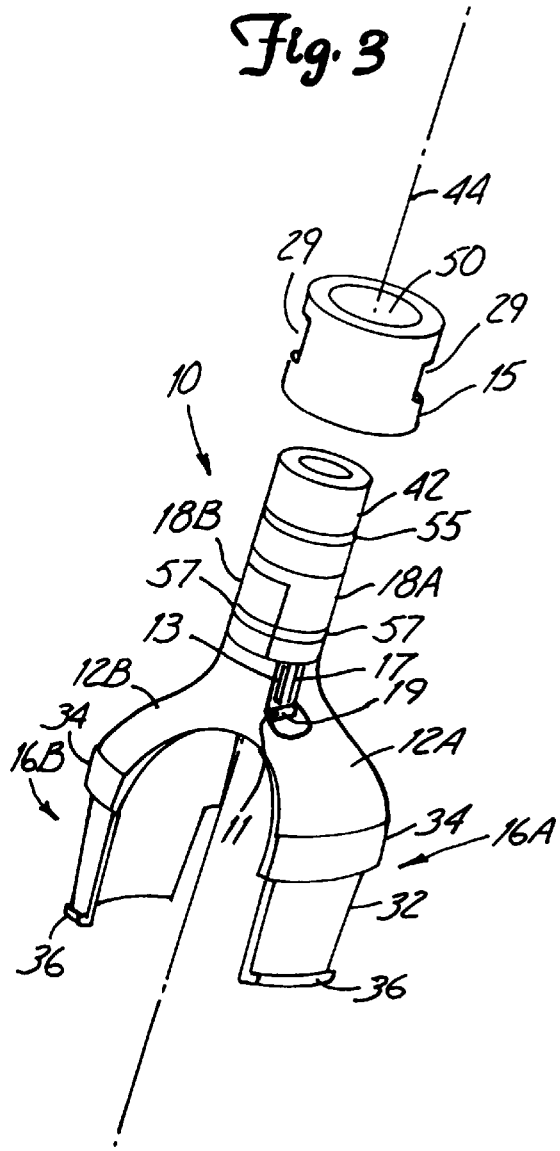
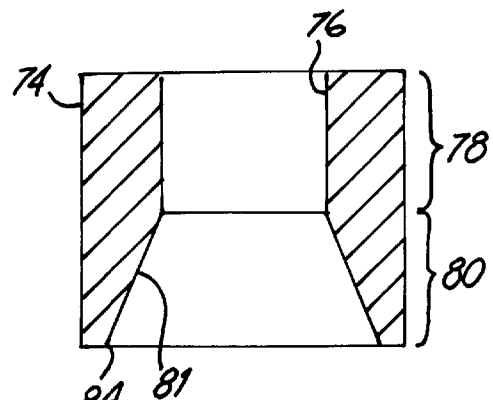
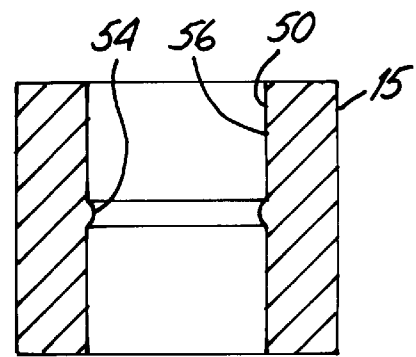
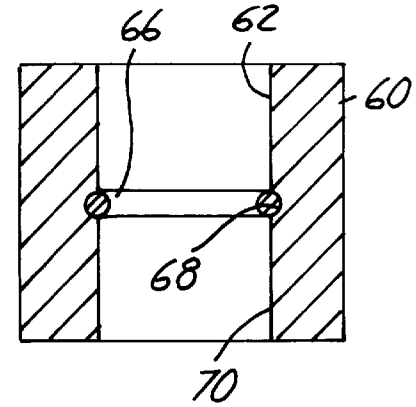

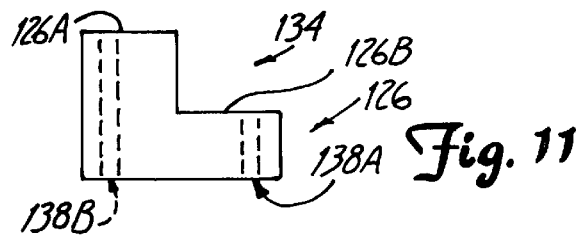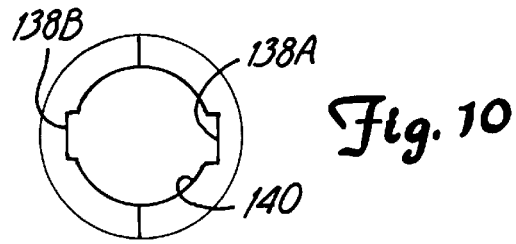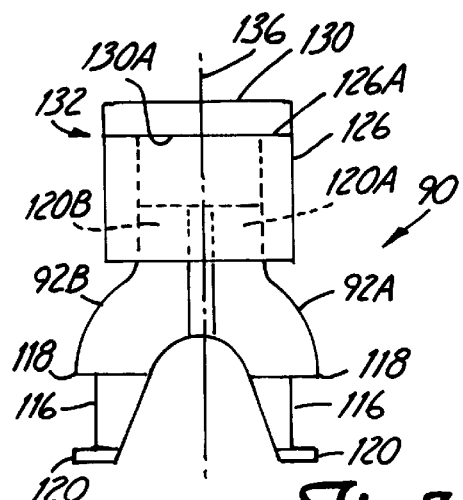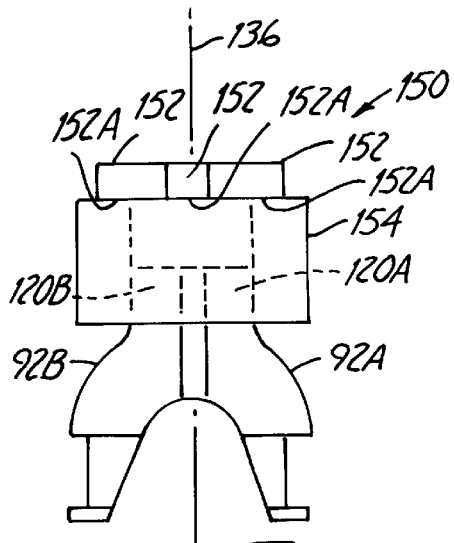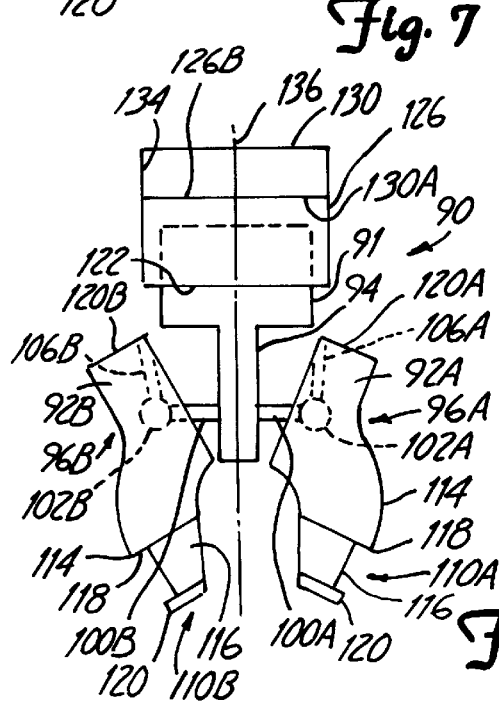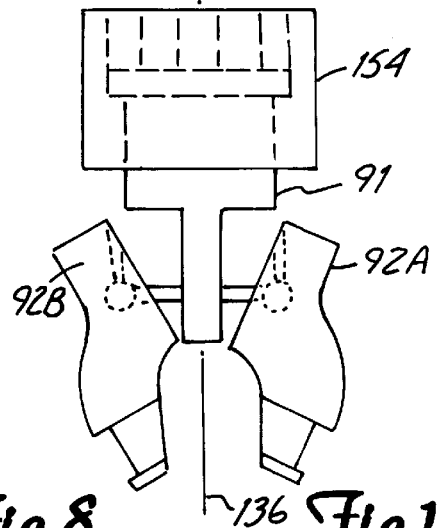

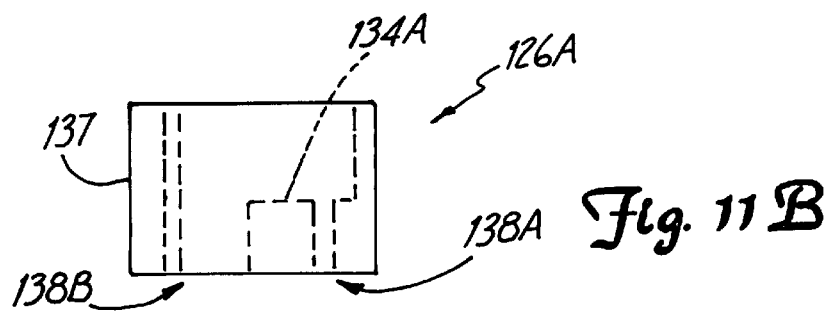
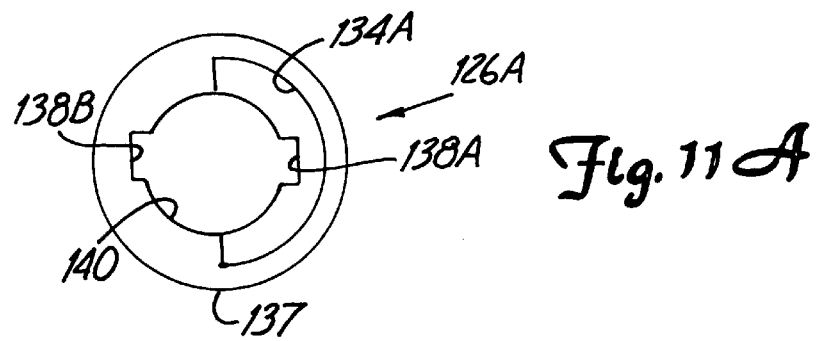
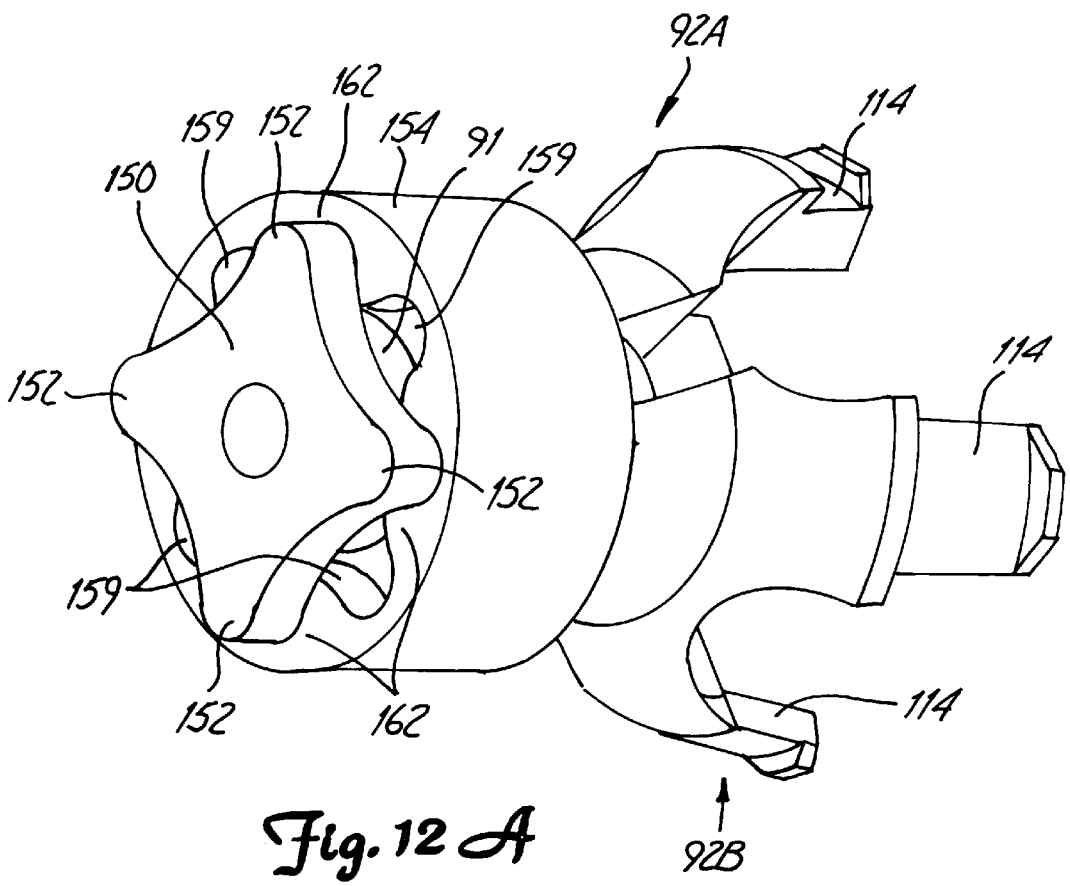

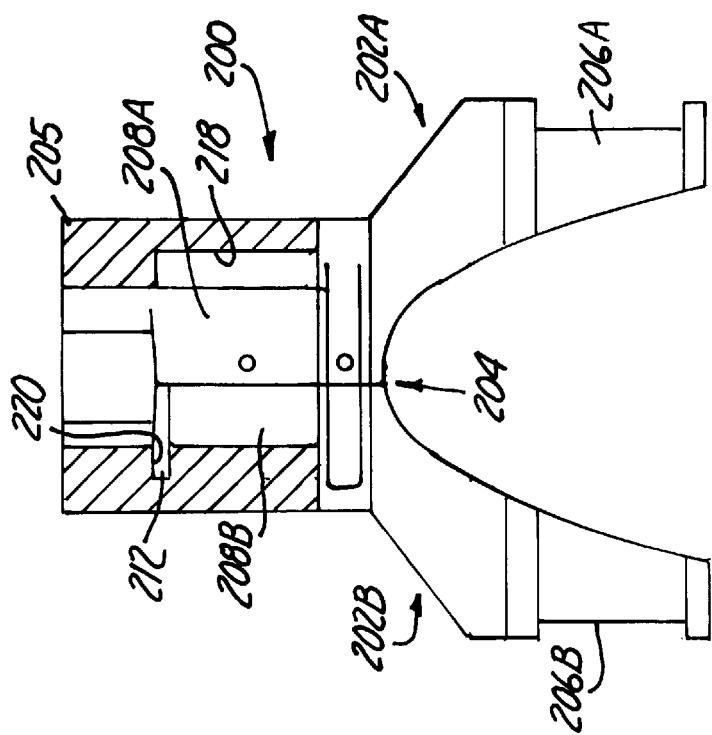
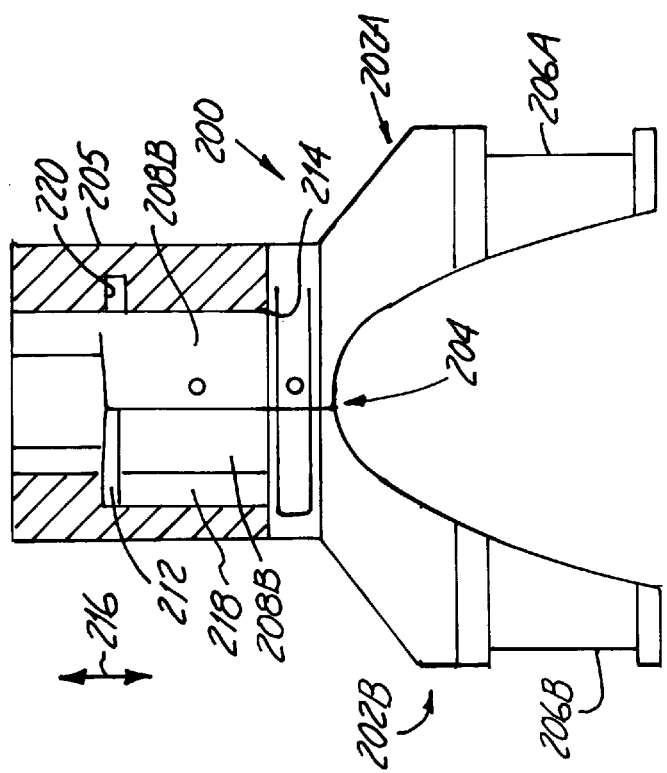

6,019,790

HEART VALVE HOLDER HAVING A LOCKING COLLAR

CROSS REFERENCE TO RELATED APPLICATIONS

This is a continuation-in-part of application Ser. No. 08/962,752 filed Nov. 3, 1997 entitled "RELEASABLE HANGER FOR HEART VALVE PROSTHESIS LOW PROFILE HOLDER", which is incorporated herein by reference, and which is a continuation application of U.S. Ser. No. 08/719,192, filed Sep. 24, 1996, now abandoned, which is a continuation-in-part of U.S. Ser. No. 08/449,145, filed May 24, 1995, now U.S. Pat. No. 5,578,076, issued Nov. 26, 1996. This is further a continuation of U.S. Ser. No. 08/730,867, filed Oct. 18, 1996, now abandoned.

FIELD OF INVENTION

The present invention relates to mechanical prosthetic heart valves. More particularly, the present invention relates to a device for holding a heart valve during manufacturing, shipping and surgical implantation of the prosthetic heart valve in the patient.

BACKGROUND OF THE INVENTION

An implantable prosthetic heart valve is used as a replacement for an excised native heart valve of a patient. A typical prosthetic heart valve includes an annular valve body to provide a passageway for blood flow. At least one, and usually two, leaflets or occluders are mounted to an inner surface of the annular valve body and open or close with the flow of blood through the passageway.

A suture ring or sewing cuff is used to sew the prosthetic heart valve to the patient's heart tissue. The sewing cuff is placed proximate the tissue annulus at the site of the excised native heart valve. The sewing cuff is secured about the annular valve body in a circumferential groove and generally includes a biocompatible fabric that allows a needle and a suture to pass through.

Holders have been developed to assist in the implantation of the prosthetic heart valve. One such holder includes two jaws linked by a hinge. Flanges on a distal end of each jaw form arcuate channels that are inserted into the passageway of the annular valve body to engage an inner circumferential surface of the annular valve body. A suture is then tied tightly around proximal ends of the jaws to hold the jaws together so that the distal ends are extended and the flanges engage the annular valve body. When the suture is cut, one or both of the jaws pivot on the hinge to move the flanges together and thereby disengage from the inner circumferential surface of the annular valve body. In this position, the holder can be retracted from the prosthetic heart valve.

Once the suture has been cut, it is quite difficult, time consuming, and in some cases impossible to reattach the prosthetic heart valve to the holder. In addition, when the suture is cut, the surgeon must ensure that the holder and suture is removed For convenience, a prosthetic heart valve and its associated holder are commonly assembled by the manufacturer and shipped in a sterile enclosure. To prevent damage to the prosthetic heart valve during shipping and handling, the assembly must form a stable structure. During shipping, the suture can elongate, become untied, or even break. When this occurs, the prosthetic heart valve may dislodge from the holder and could be damaged.

SUMMARY OF THE INVENTION

A prosthetic heart valve holder includes a set of jaws. Each jaw includes a distal end adapted for coupling to the prosthetic heart valve and a proximal end. A hinge assembly pivotally couples the jaws together between the distal and proximal ends. The hinge assembly allows relative movement of the jaws between an engaged position for grasping the prosthetic heart valve and a disengaged position in which the prosthetic heart valve is free from the distal ends of the holder. A locking collar is attached to the jaws and is movable between a first position in which the proximal ends of the jaws are free from the collar, and a second position in which the collar is positional around and holds the proximal ends of the jaws such that the distal ends are held in position to engage the prosthetic heart valve.

BRIEF DESCRIPTION OF THE DRAWINGS

FIG. 3 is an exploded perspective view of the holder of FIG. 1.

FIG. 4 is a sectional view of a locking collar.

FIG. 5 is a sectional view of a second embodiment of a locking collar.

FIG. 6 is a sectional view of a third embodiment of a locking collar.

FIG. 7 is a schematic front elevational view of a second embodiment of a holder of the present invention in an engaged position.

FIG. 8 is a schematic front elevational view of the holder of FIG. 7 in a disengaged position.

FIG. 10 is a top plan view of a fourth embodiment of a locking collar.

FIG. 11 is a side elevational view of the locking collar of FIG. 10.

FIG. 11A is a top plan view of an alternate embodiment of the locking collar of FIG. 10.

FIG. 11B is a side elevational view of the locking collar of FIG. 11A.

FIG. 12 is a schematic front elevational view of a third embodiment of a holder of the present invention in an engaged position.

FIG. 12A is a schematic perspective view of the third embodiment of FIG. 12 in the engaged position.

FIG. 13 is a schematic front elevational view of the holder of FIG. 12 in a disengaged position.

FIG. 23 is a front elevational view of the holder of FIG. 22 in an engaged position.

FIG. 24 is a front elevational view of the holder of FIG. 22 in a locked position.

DETAILED DESCRIPTION OF THE PREFERRED EMBODIMENTS

Figure 1:
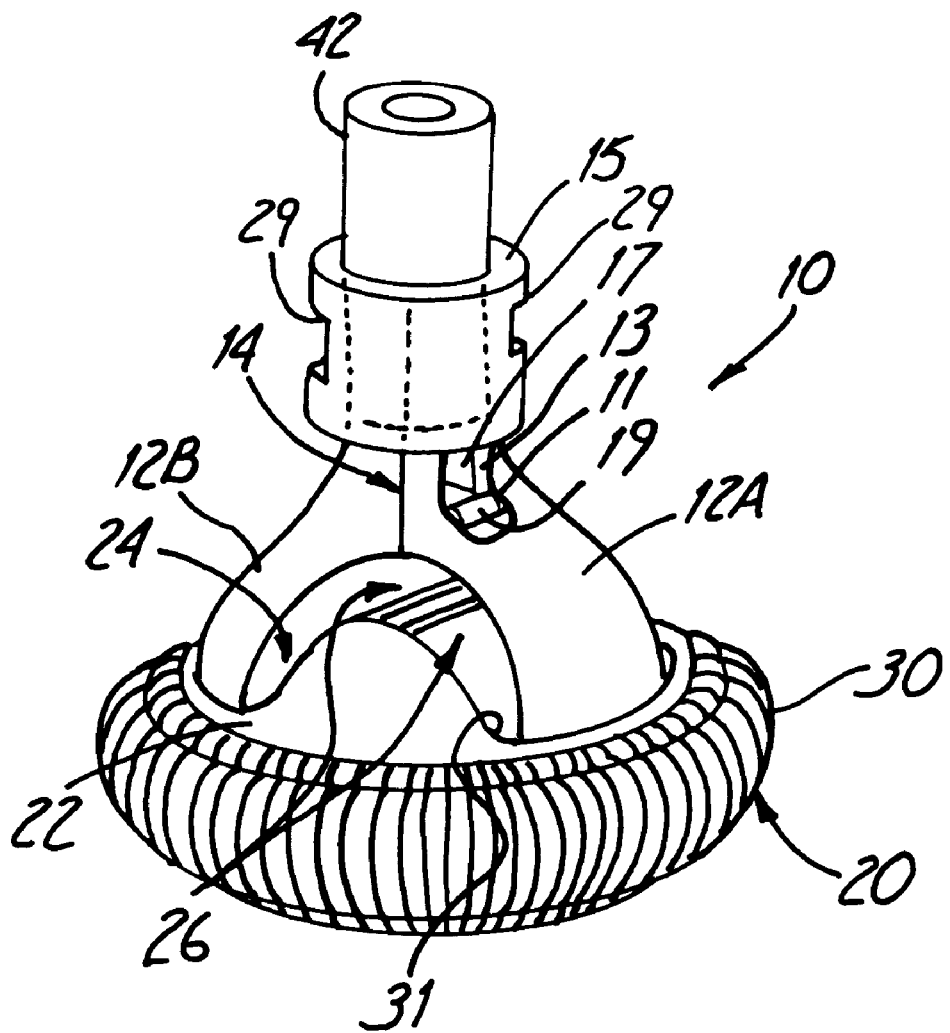
FIG. 1 is a perspective view of a first embodiment of a holder of the present invention and a prosthetic heart valve.
Figure 2:
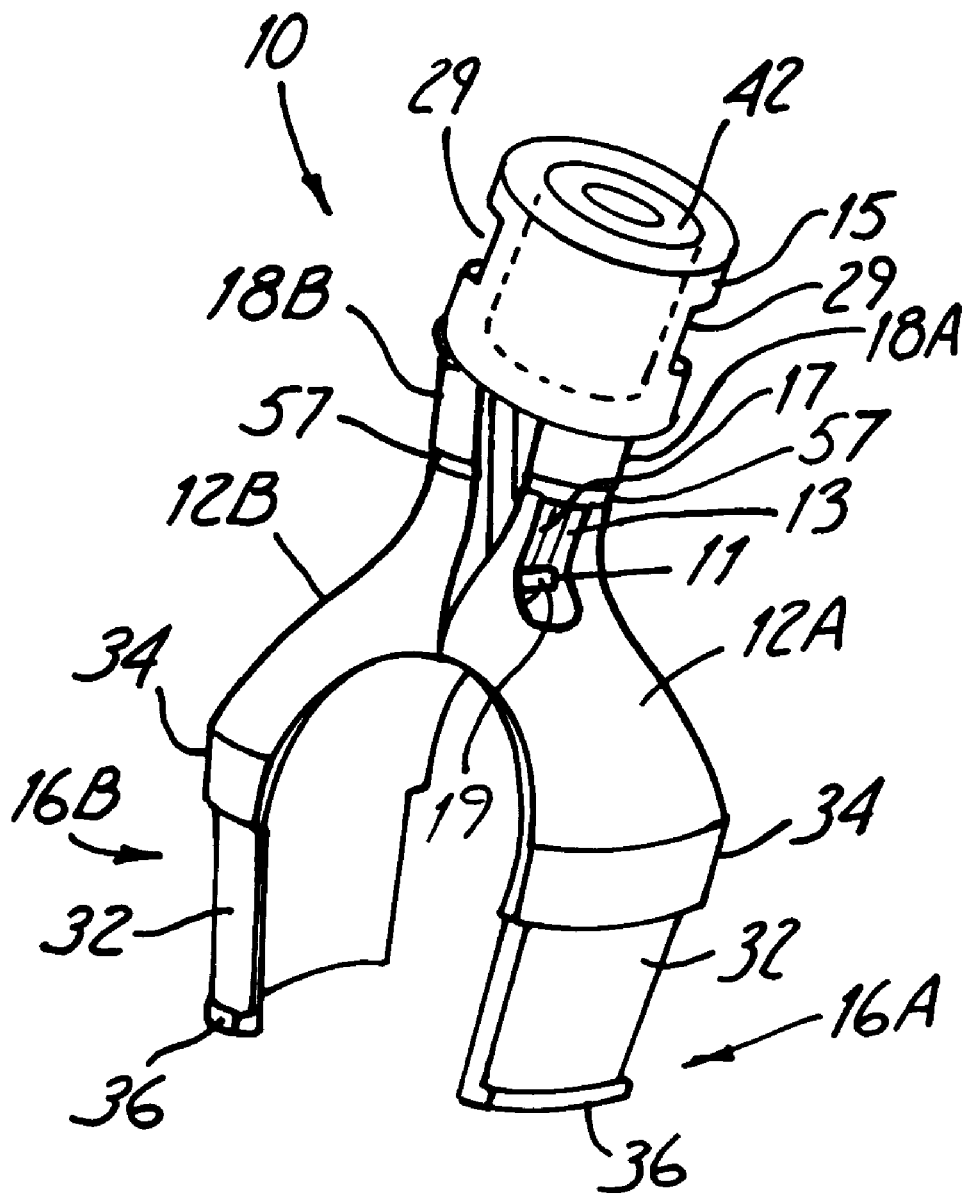
FIG. 2 is a perspective view of the holder of FIG. 1 in a disengaged position.

FIGS. 1, 2 and 3 illustrate a first embodiment of a prosthetic heart valve holder of the present invention generally at 10. The holder 10 includes a set of jaws 12A and 12B pivotally joined together with a hinge assembly 14. The jaws 12A and 12B selectively engage a prosthetic heart valve 20 by pivoting on the hinge assembly 14. A locking collar 15 selectively locks pivotal movement of the jaws 12A and 12B.

In this embodiment, the hinge assembly 14 includes a crossbar 11 secured to jaw 12B that extends into an aperture 13 in jaw 12A. A resilient spring bar 17 retains a head 19 of the crossbar 11 within the aperture 13. It should be understood that the hinge assembly 14 is but one embodiment of a hinge assembly. Other known hinge type mechanisms such as forms of pins or flexible webs can also be used.

Briefly, the prosthetic heart valve 20 includes an annular valve body 22 forming a passageway 24 for the flow of blood and one or more hinged "leaflets" or occluders 26 that pivot to control the flow of blood through the passageway 24. A sewing cuff 30 is used to secure the prosthetic heart valve 20 to the patient's heart tissue. The sewing cuff 30 is secured about the annular valve body 22 and generally includes a biocompatible fabric suitable for allowing a needle and a suture to pass through. FIG. 1 illustrates a mitral prosthetic heart valve. The present invention may be used with either mitral or aortic heart valves.

The jaws 12A and 12B are similar to each other. Referring also to FIGS. 2 and 3, distal ends 16A and 16B of the jaws 12A and 12B, respectively, are adapted to engage an inner circumferential surface 31 of the annular valve body 22. Each distal end 16A and 16B includes an arcuate support plate 32 and arcuate flanges 34 and 36 disposed on opposite sides of the arcuate support plate 32. As illustrated in FIG. 1, the distal ends 16A and 16B are each located between an occluder 26 and a portion of the inner circumferential surface 31. With pivoting movement of the jaws 12A and 12B on the hinge assembly 14, the distal ends 16A and 16B move within the space between the occluders 26 and the inner circumferential surface 31 to engage the annular valve body 22. When proximal ends 18A and 18B of the jaws 12A and 121 are held fixed relative to each other, the distal ends 16A and 16B engage the inner circumferential surface 31 to hold the prosthetic heart valve 20. When the proximal ends 18A and 18B are free to move, the distal ends 16A and 16B release from the inner circumferential surface 31, allowing the holder 10 to be withdrawn from the prosthetic heart valve 20.

The locking collar 15 selectively inhibits pivotal movement of the proximal ends 18A and 18B. The locking collar 15 is movable between a first position illustrated in FIG. 2 in which the proximal ends 18A and 18B are free from the locking collar 15 to pivot relative to each other, and a second position, illustrated in FIG. 1, in which the locking collar 15 holds the proximal ends 18A and 18B such that the distal ends 16A and 16B are held in position to engage the annular valve body 22. Unlike prior art techniques that use a suture tied around the proximal ends of jaws of other holders, the locking collar 15 allows quick and easy re-engagement of the holder 10 with the prosthetic heart valve 20, if desired. Suitable grooves or recesses 29 can be provided in the locking collar 15 as desired to allow the holder 10, as well as the other holder embodiments shown herein, to be suspended in sterilized shipping container, not shown.

In the embodiment illustrated in FIGS. 1–3, the jaw 12A includes an extending portion 42 adapted for connection to a handle, not shown. The locking collar 15 is movable along and parallel to an axis 44 of the holder 10. In the first position illustrated in FIG. 2, the locking collar 15 is disposed about the extending portion 42 of the jaw 12A, while in the second position illustrated in FIG. 1, the proximal end 18B of the jaw 12A is disposed below a portion of the extending portion 42 such that the collar 15 fits around the proximal ends 18A and 18B.

Referring also to FIG. 4, the locking collar 15 includes an inner bore 50 of size and shape corresponding to the extending portion 42 and the proximal ends 18A and 18B when joined together. In the embodiment illustrated, the bore 50 is cylindrical. However, the bore 50 can be rectangular, oval, or other shapes, depending on the shape of the extending portion 42. In addition, the outside of locking collar 15 can be of any shape to facilitate handling.

If desired, as illustrated in FIG. 4, the locking collar 15 can include a detent mechanism to provide a tactile indication to the operator of when the first position of the locking collar 15 and the second position of the locking collar 15 are obtained. The detent mechanism also inhibits removal of the locking collar 15 from the extending portion 42 when the jaws 12A and 12B are free to move. In the embodiment illustrated, the detent mechanism includes a protrusion such as an annular ring 54 formed on an inner surface 56 of the bore 50. The annular ring 54 selectively engages an annular recess 55 provided on the extending portion 42, or arcuate recesses 57 on and the proximal ends 18A and 18B as illustrated in FIG. 3. Of course, if desired, the protrusions can be formed on the extending portion 42 and the proximal ends 18A and 18B with corresponding recesses provided on the inner surface 56 of the bore 50.

The holder 10, and other embodiments of holders of the present invention described below, can be formed from any suitable material, for example, plastic, such as polysulfone, or metal using conventional molding or machining techniques. The locking collar 15 can be machined of a hard thermoplastic material, such as polysulfone or molded from a softer material such as silicone rubber, which can increase friction and provides a tighter fit between the locking collar 15 and proximal ends 18A and 18B.

Another embodiment of a locking collar 60 is illustrated in FIG. 5. The locking collar 60 is similar to the locking collar 15 and includes a bore 62 slidable over the extending portion 42 and the proximal ends 18A and 18B. In this embodiment, an o-ring 66 is disposed within the bore 62 to increase the sliding friction of the locking collar 60 over the extending portion 42 and the proximal ends 18A and 18B. The o-ring 66 is disposed in an annular recess 68 provided on an inner surface 70.

FIG. 6 illustrates yet another embodiment of a locking collar 74. The locking collar 74 includes a bore 76 having a section of constant width indicated at 78 and a tapered section indicated at 80. In the embodiment illustrated, the constant width section 78 is generally circular having an inner diameter slightly larger than the diameter of the extending portion 42 and the proximal ends 18A and 18B when joined together. In contrast, the tapered section 80 has an opening 84 that is substantially larger than the diameter of the extending portion 42 and the proximal ends 18A and 18B when joined together. A tapered inner surface 81 of the tapered section 80 guides the proximal ends 18A and 18B together as the locking collar 74 is slid down from the extending portion 42 and allows the locking collar 74 to seat better on the tapered surfaces of the jaws 12A and 12B. In the embodiment illustrated, the tapered inner surface 81 is generally conical.

Figure 7A:
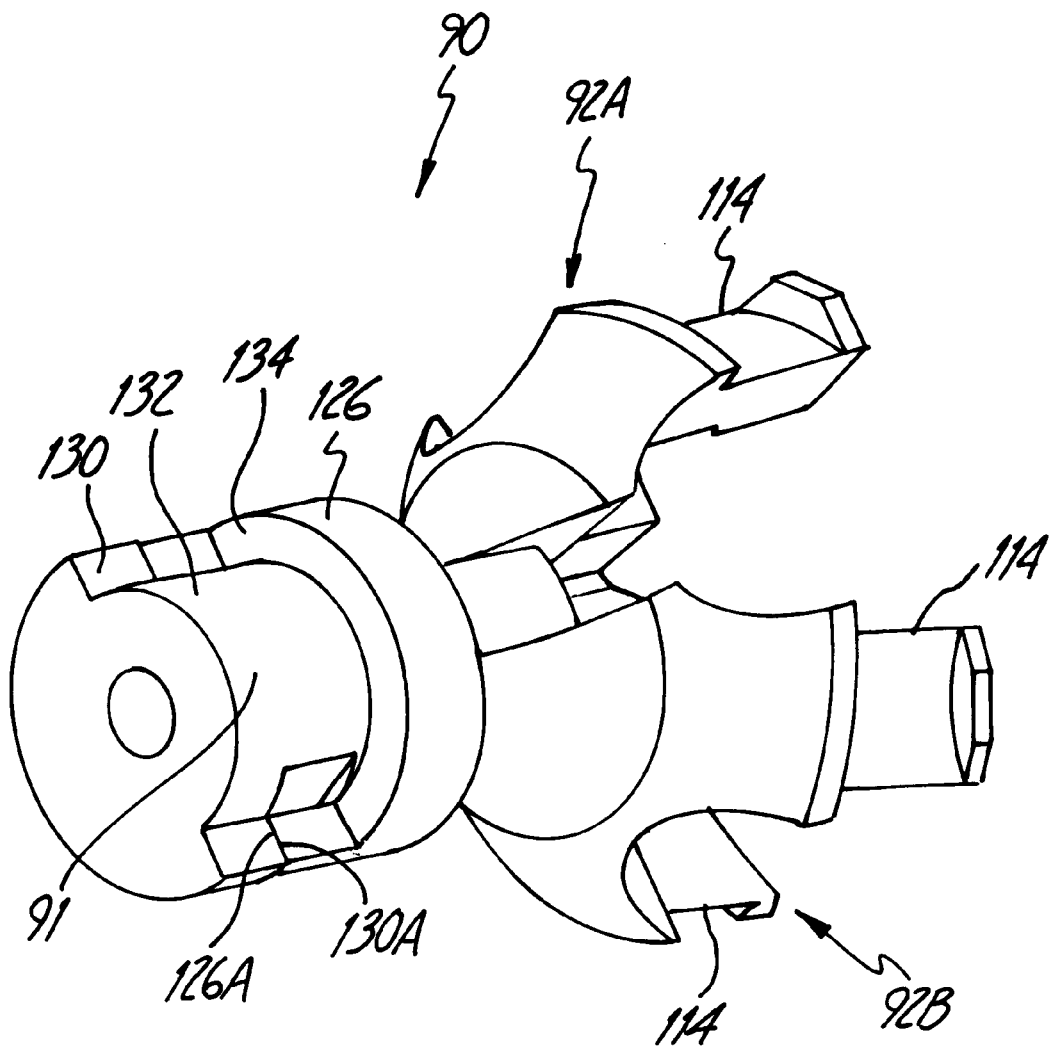
FIG. 7A is a schematic perspective view of the second embodiment of FIG. 7 in the engaged position.
Figure 8A:
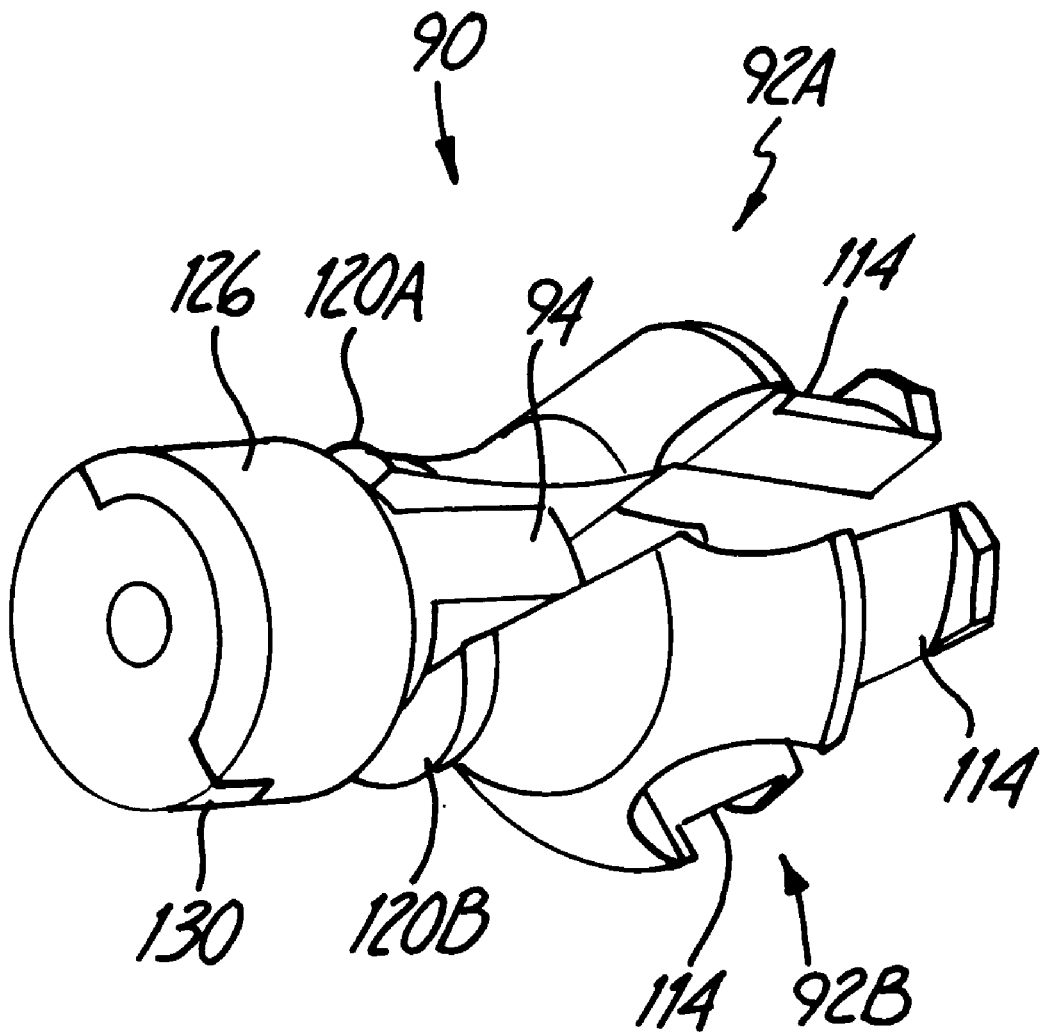
FIG. 8A is a schematic perspective view of the second embodiment of FIG. 7 in the disengaged position.
Figure 9:
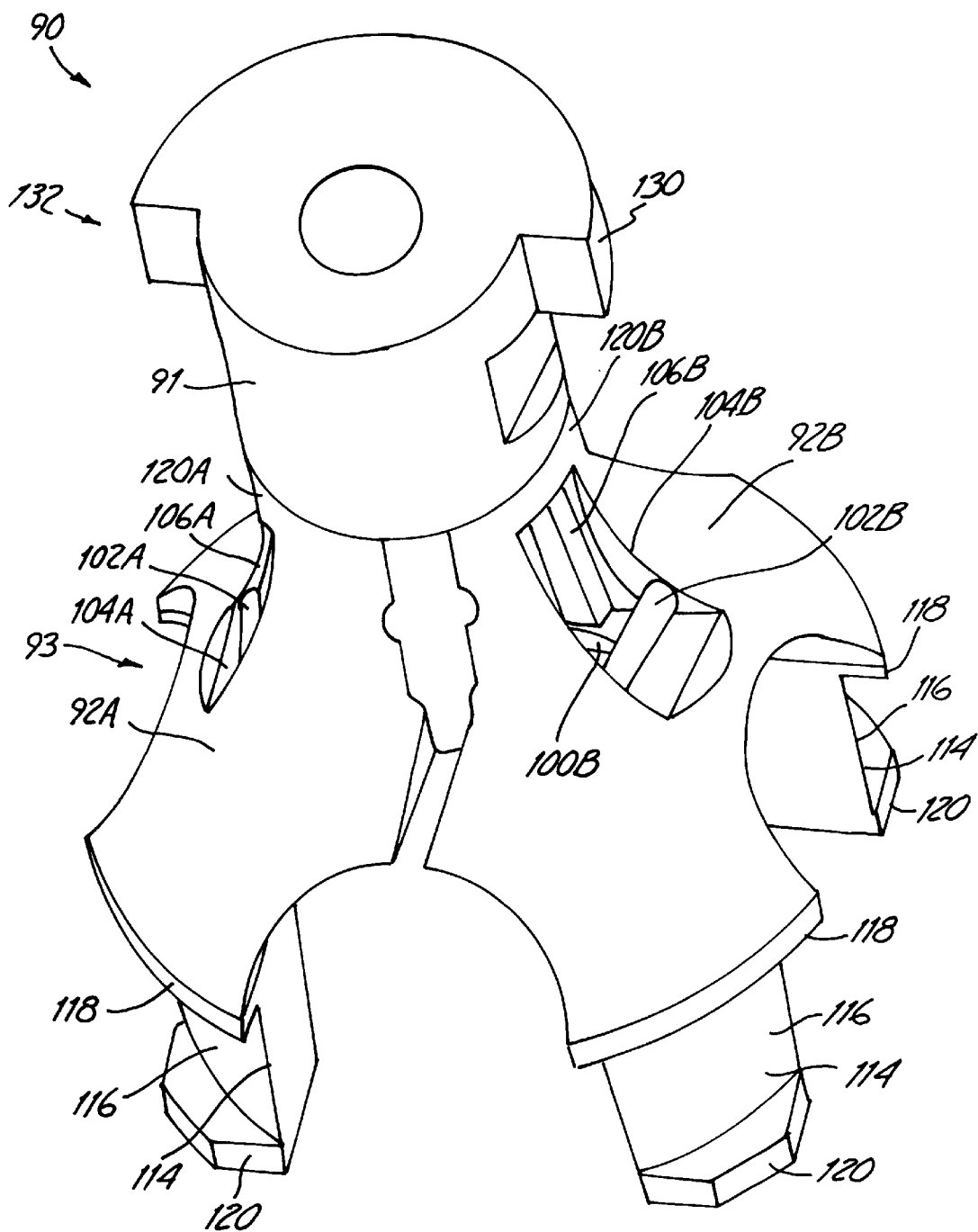
FIG. 9 is a perspective view of the holder of FIG. 7 without a locking collar.

Another embodiment of a holder 90 of the present invention is illustrated in FIGS. 7, 7A, 8, 8A and 9. The holder 90 includes a stem 91 and a set of jaws 92A and 92B pivotally joined to a distal end 94 of the stem 91 with a hinge assembly 93 as shown in FIG. 9. Referring to FIG. 8, the hinge assembly 93 includes a hinge 96A formed between the stem 91 and the jaw 92A and a hinge 96B formed between the stem 91 and the jaw 92B. The hinge 96A includes a support 100A extending outwardly from the distal end 94 of stem 91. A crossbar 102A is secured to a remote end of the support 100A. The jaw 92A includes an aperture 104A that receives the crossbar 102A shown in FIG. 9. A resilient spring bar 106A contacts the crossbar 102A to inhibit removal of the jaw 92A from the stem 91.

The hinge 96B is similarly constructed between the jaw 92B and the stem 91. The hinge 96B includes a support 100B and a crossbar 102B. The crossbar 102B is received through an aperture 104B in the jaw 92B. A resilient spring bar 106B engages the crossbar 102B to inhibit removal of the jaw 92B from the stem 91.

Distal ends 110A and 110B of the jaws 92A and 92B, respectively, are adapted to engage the inner circumferential surface 31 of the annular valve body 22 illustrated in FIG. 1. Each distal end 110A and 110B includes two spaced-apart extending supports 114. Each extending support 114 includes an arcuate support plate 116 and flanges 118 and 120 disposed on opposite sides of the arcuate support plate 116. The extending supports 114 engage the inner circumferential surface 31 of the annular valve body 22 when proximal ends 120A and 120B of the jaws 92A and 92B, respectively, are held fixed relative to each other. As illustrated, the proximal ends 120A and 120B are disposed below a portion 122 of the stem 91.

Referring to FIGS. 7, 7A, 8, 8A, 10 and 11, a locking collar 126 selectively inhibits pivotal movement of the proximal ends 120A and 120B. The locking collar 126 is movable between a first position illustrated in FIGS. 8 and 8A in which the proximal ends 120A and 120B are free from the locking collar 126 to pivot, and a second position, illustrated in FIGS. 7 and 7A, in which the locking collar 126 holds the proximal ends 120A and 120B such that the extending supports 114 are held in position to engage the annular valve body 22.

An extending flange 130 is provided on an end 132 of the stem 91 to selectively inhibit sliding movement of the locking collar 126 over the end 132 and retain the locking collar 126 in the second or engaged position. Referring to FIGS. 7 and 7A, an end surface portion 126A of the locking collar 126 engages a stop surface 130A of the flange 130 in the second position. The locking collar 126 further includes a cutout 134 of size and shape to receive the extending flange 130 when the locking collar 126 has been rotated about an axis 136 of the stem 91 as illustrated in FIGS. 8 and 8A. In other words, the cutout 134 of the locking collar 126 is keyed to the extending flange 130. In this manner, the locking collar 126 can be slid along the stem 91 so that the extending flange 130 is received by the cutout 134 and an end surface portion 126B is positioned proximate the stop surface 130A of the flange 130. In this position, the proximal ends 120A and 120B are free to pivot, allowing the extending supports 114 to release from a prosthetic heart valve, not shown.

The holder 90 is assembled by sliding the locking collar 126 over the distal end 94 of the stem 91. Referring to FIGS. 10 and 11, opposed recesses 138A and 138B of an inner bore 140 are provided such that a width between the crossbars 102A and 102B exceeds a diameter of the stem 91. After the locking collar 126 has been positioned on the stem 91, the jaws 92A and 92B are snapped onto the stem 91 to form the hinges 96A and 96B. Alternatively, a pin could be used to attach jaw 92A and 92B to the stem 91.

FIGS. 11A and 11B illustrate an alternate locking collar 126A suitable for use on the stem 91 of the holder 90. The alternate locking collar 126A does not have a cutout 134 to receive the extending flange 130, but rather, a recess 134A of size and shape to receive the extending flange 130. In the embodiment illustrated, an outer surface 137 is generally cylindrical, allowing the alternating locking collar 126A to be easily gripped and manufactured. Of course, other outer surface configurations can also be used.

Figure 15:
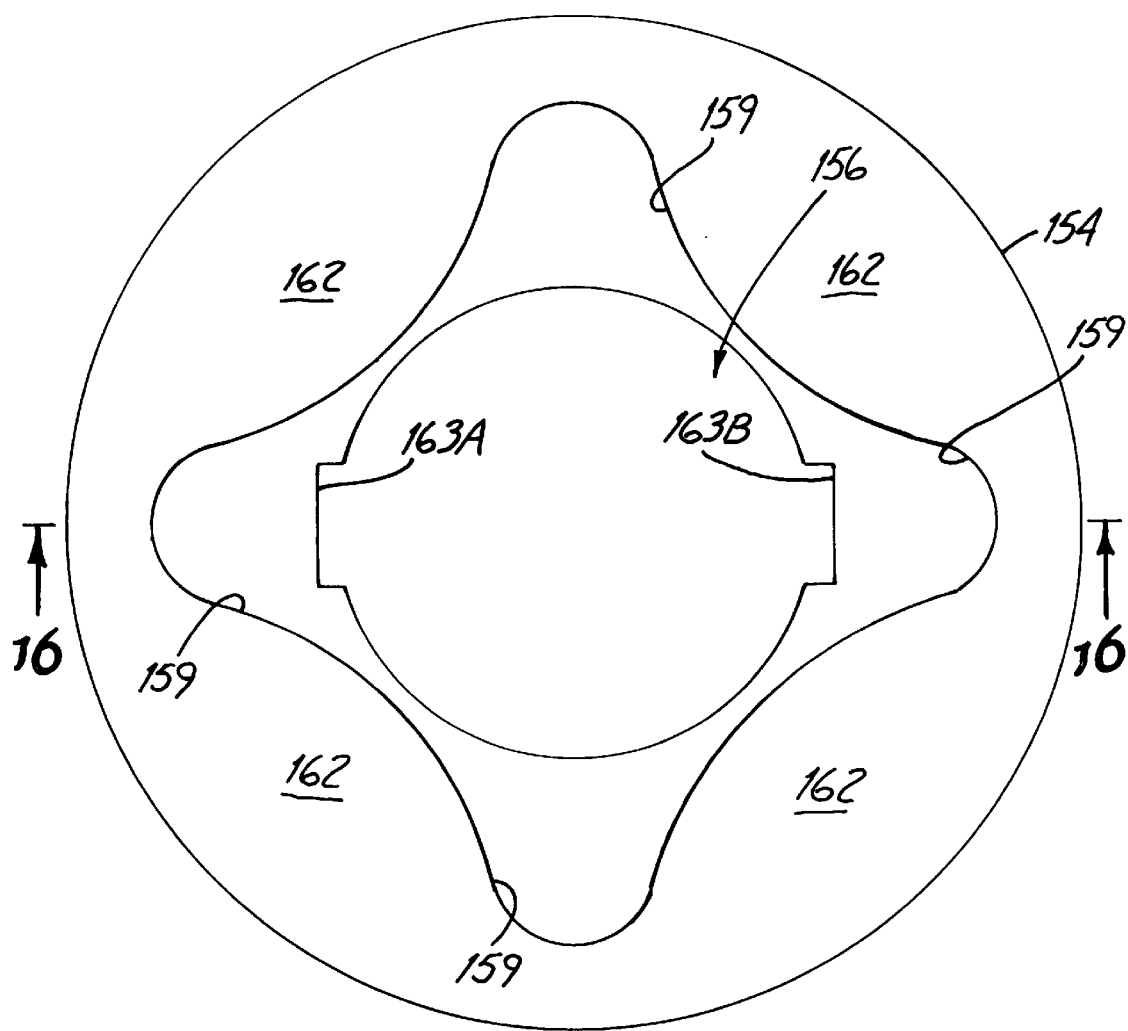
FIG. 15 is a top plan view of a fifth embodiment of a locking collar.
Figure 16:
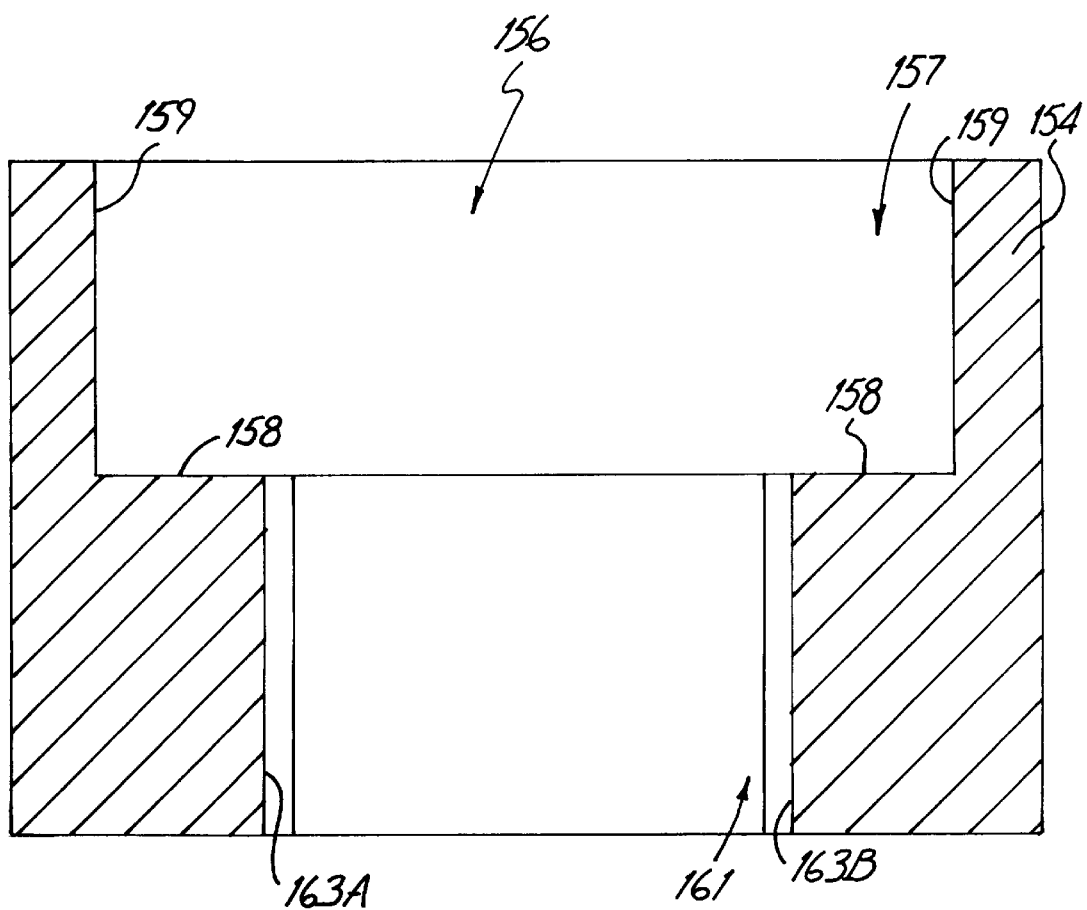
FIG. 16 is a sectional view of the locking collar taken along lines 16—16 in FIG. 15.

In FIGS. 12, 12A, 13, 13A and 14, an extending flange 150 is formed with multiple spaced-apart protrusions 152. A locking collar 154 slides along the stem 91 and selectively inhibits pivotal movement of the proximal ends 120A and 120B. Referring also to FIGS. 15 and 16, an inner bore 156 of the locking collar 154 includes a first portion 157 having recesses 159 adapted or keyed to receive the protrusions 152 of the extending flange 150 so that the locking collar 154 can be slid along the stem 91 in order to free the proximal ends 120A and 120B. Preferably, a surface 158 is formed within the locking collar 154 and engages stop surfaces 152A on the protrusions 152 to limit sliding movement of the locking collar 154. A second portion 161 of the bore 156 is of size slightly larger than the stem 91 and includes recesses 163A and 163B similar to recesses 138A and 138B.

The proximal ends 120A and 120B are held fixed relative to each other when the locking collar 154 is slid along the stem 91 toward the extending supports 114. Rotation of the locking collar 154 about the axis 136 of the stem 91 positions end surface portions 162 of the locking collar 154 opposite the stop surfaces 152A (FIG. 12) of the protrusions 152 in order to inhibit sliding movement of the locking collar 154 on the stem 91 and retain the locking collar 154 in the second or engaged position.

Figure 13A:
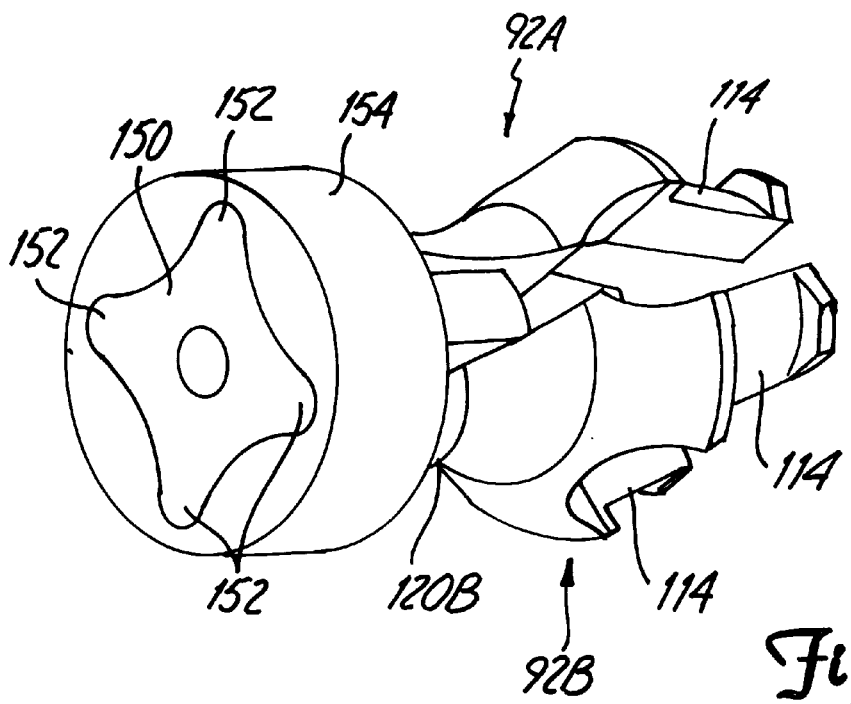
FIG. 13A is a schematic perspective view of the holder of FIG. 12 in the disengaged position.
Figure 13B:
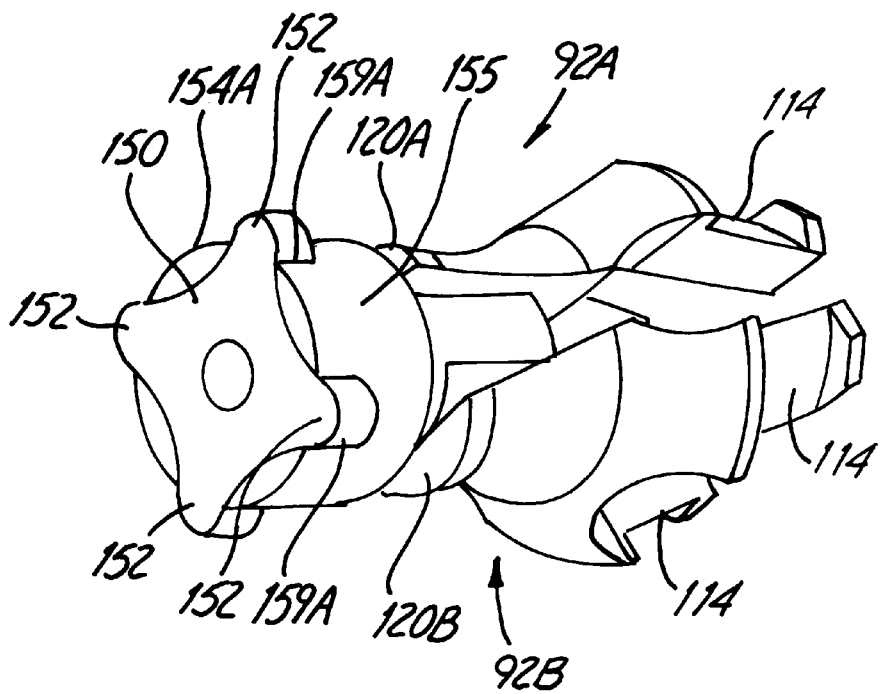
FIG. 13B is a schematic perspective view of an alternate embodiment of the holder of FIG. 12.
Figure 14:
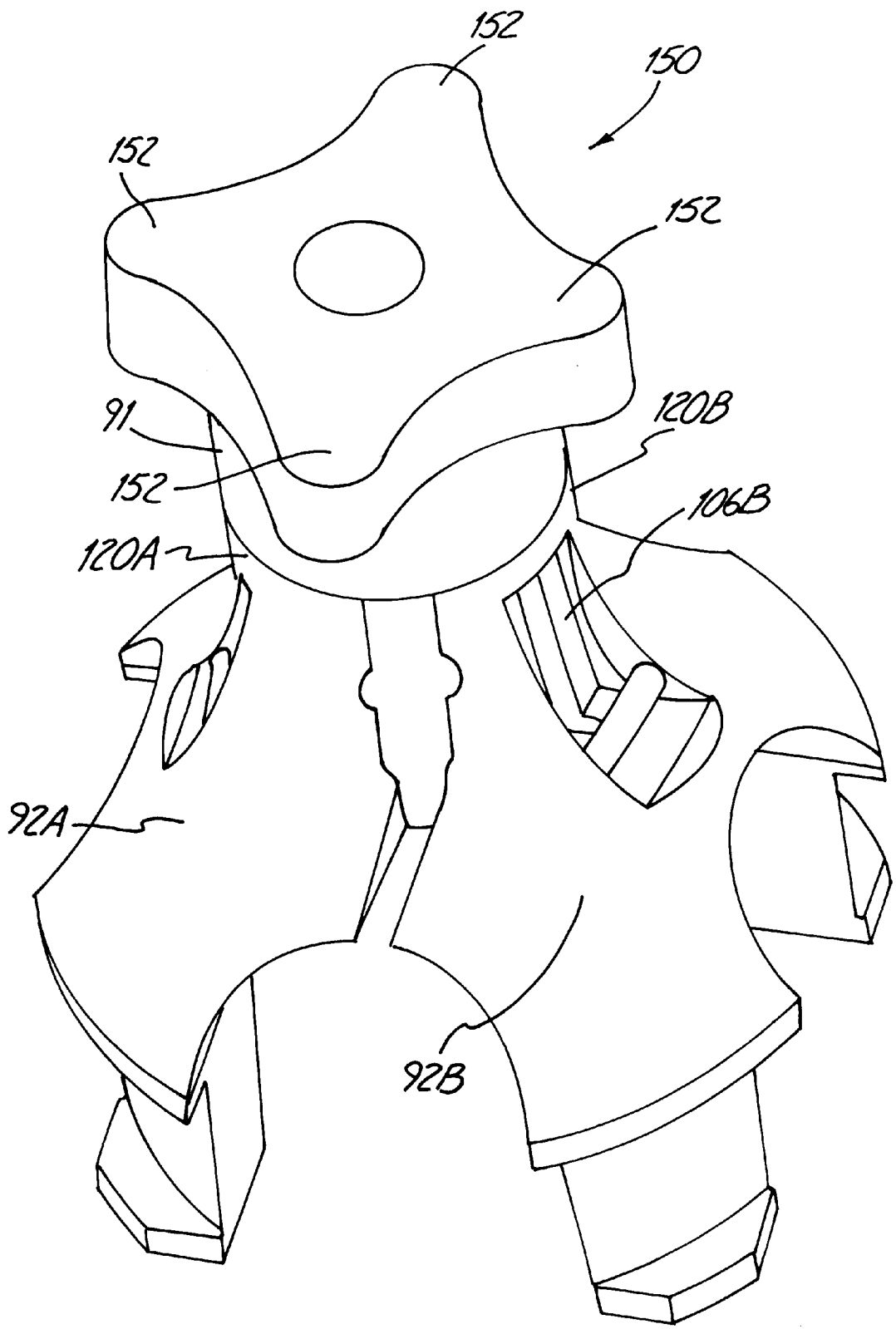
FIG. 14 is a perspective view of the holder of FIG. 12 without a locking collar.

Another embodiment of a locking collar 154A suitable for use with the holder illustrated in FIG. 13A is illustrated in FIG. 13B. The locking collar 154A has a diameter less than a diameter of the locking collar 154 such that recesses 159A open to an outer surface 155 of the locking collar 154A. In the disengaged position of FIG. 13B, the recesses 159A receive the protrusions 152 of the extending flange 150.

Figure 17:
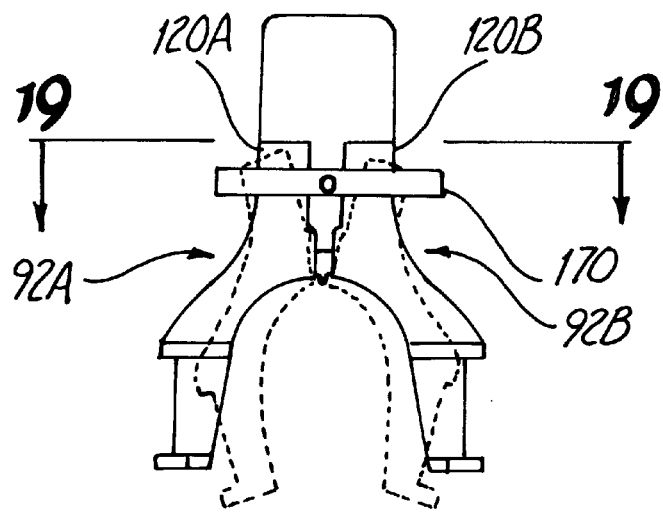
FIG. 17 is a front elevational view of a holder with a sixth embodiment of a locking collar.
Figure 18:
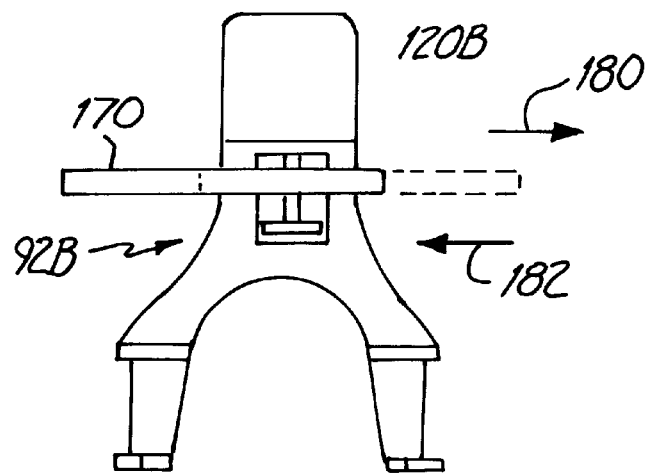
FIG. 18 is a side elevational view of the holder of FIG. 17.
Figure 19:
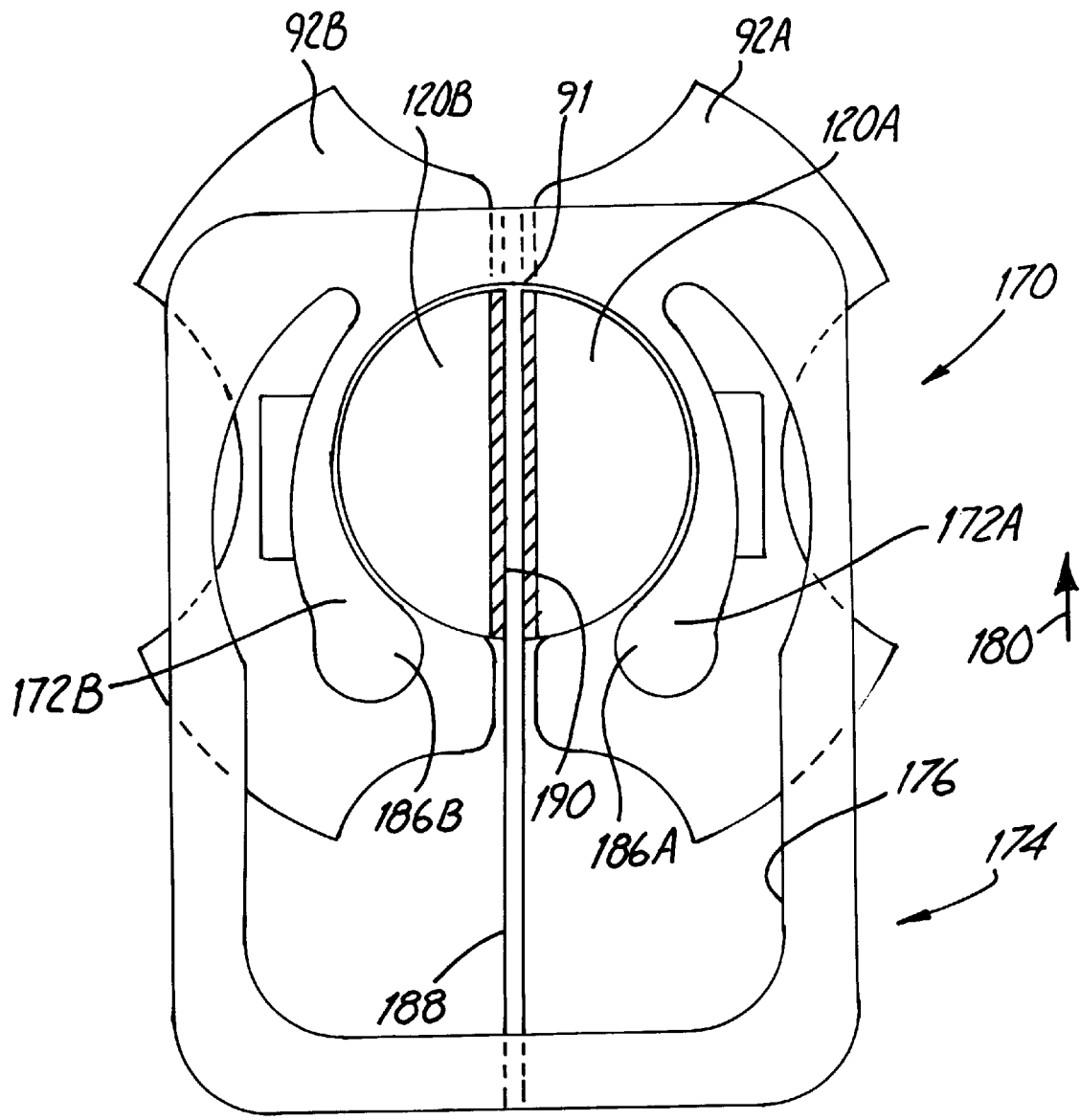
FIG. 19 is a sectional view of the holder of FIG. 17 taken along lines 19—19.
Figure 20:
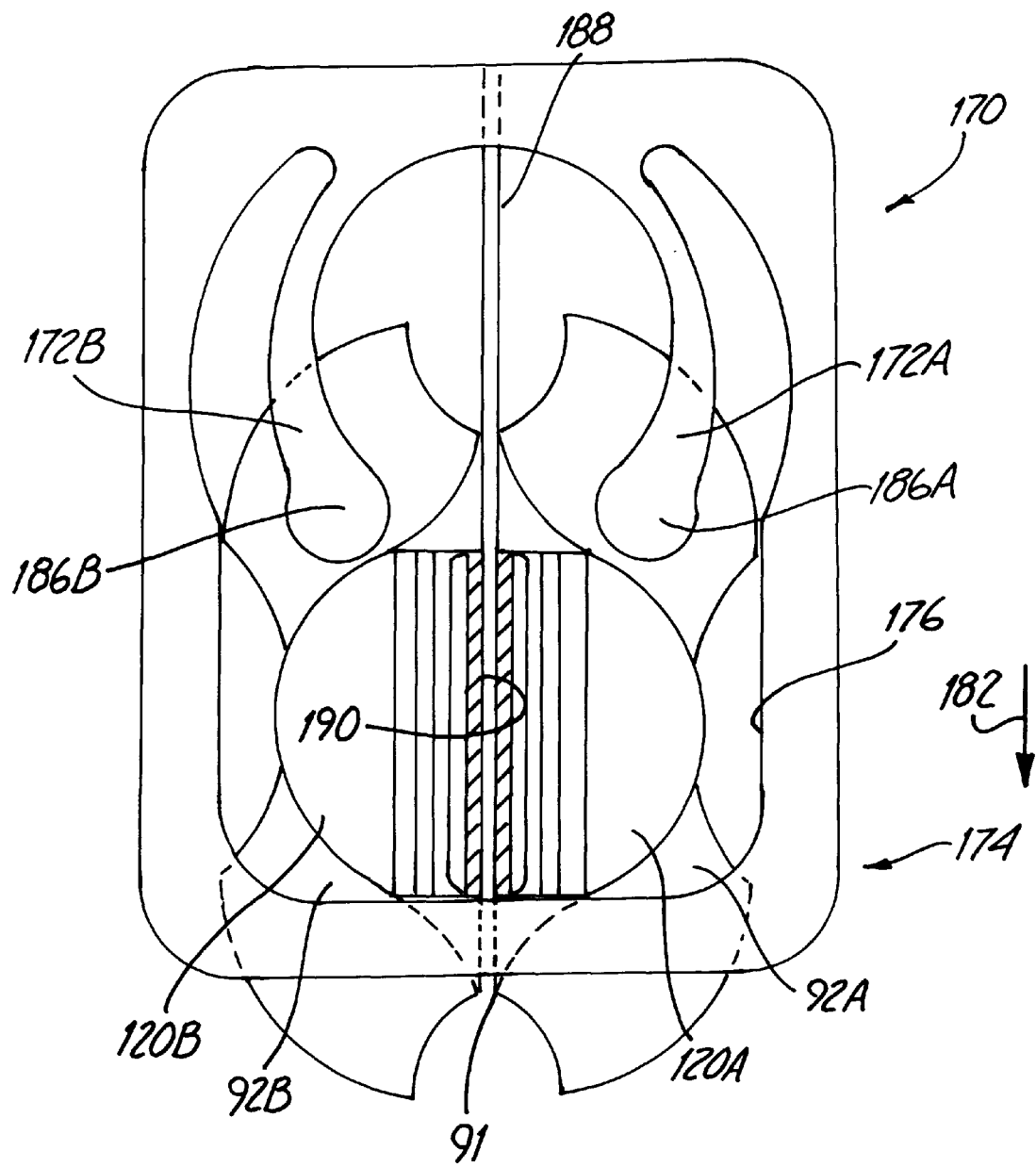
FIG. 20 is a sectional view of the holder of FIG. 17 in a disengaged position.

Another embodiment of a locking collar 170 is illustrated in FIGS. 17, 18, 19 and 20. Referring first to FIGS. 19 and 20, the locking collar 170 includes resilient members 172A and 172B that hold the proximal ends 120A and 120B in a fixed position. The locking collar 170 includes a support structure 174 forming an aperture 176. The resilient members 172A and 172B extend into the aperture 176 and are preferably formed integral with the support structure 174. In an engaged position illustrated with solid lines in FIGS. 17 and 18 and in FIG. 19, the resilient members 172A and 172B substantially surround the proximal ends 120A and 120B to hold the proximal ends 120A and 120B against the stem 91.

Movement of the locking collar 170 in a direction indicated by arrow 180 positions the locking collar 170 as illustrated with dashed lines in FIGS. 17 and 18, and in FIG. 20. In this position, the jaws 92A and 92B can freely pivot on the hinges 96A and 96B. When the locking collar 170 is displaced in a direction indicated by arrow 182, the resilient members 172A and 172B expand to allow the proximal ends 120A and 120B to slide between them. Enlarged heads 186A and 186B on the resilient members 172A and 172B, respectively, guide the proximal ends 120A and 120B toward each other and into the engaged position of FIG. 19.

Preferably, the locking collar 170 includes a pin 188 extending between opposite sides of the support structure 174 and through a bore 190 provided in the stem 91. The pin 188 guides the support structure 174 so that the extending resilient members 172A and 172B remain aligned with the proximal ends 120A and 120B. In addition, the pin 180 prevents the locking collar 170 from sliding along an axis of the stem 91. Preferably, the pin 188 is orthogonal to the axis of the stem 91; however, non-orthogonal orientation of the pin 188 with the axis of the stem 91 can also be used.

Figure 21:
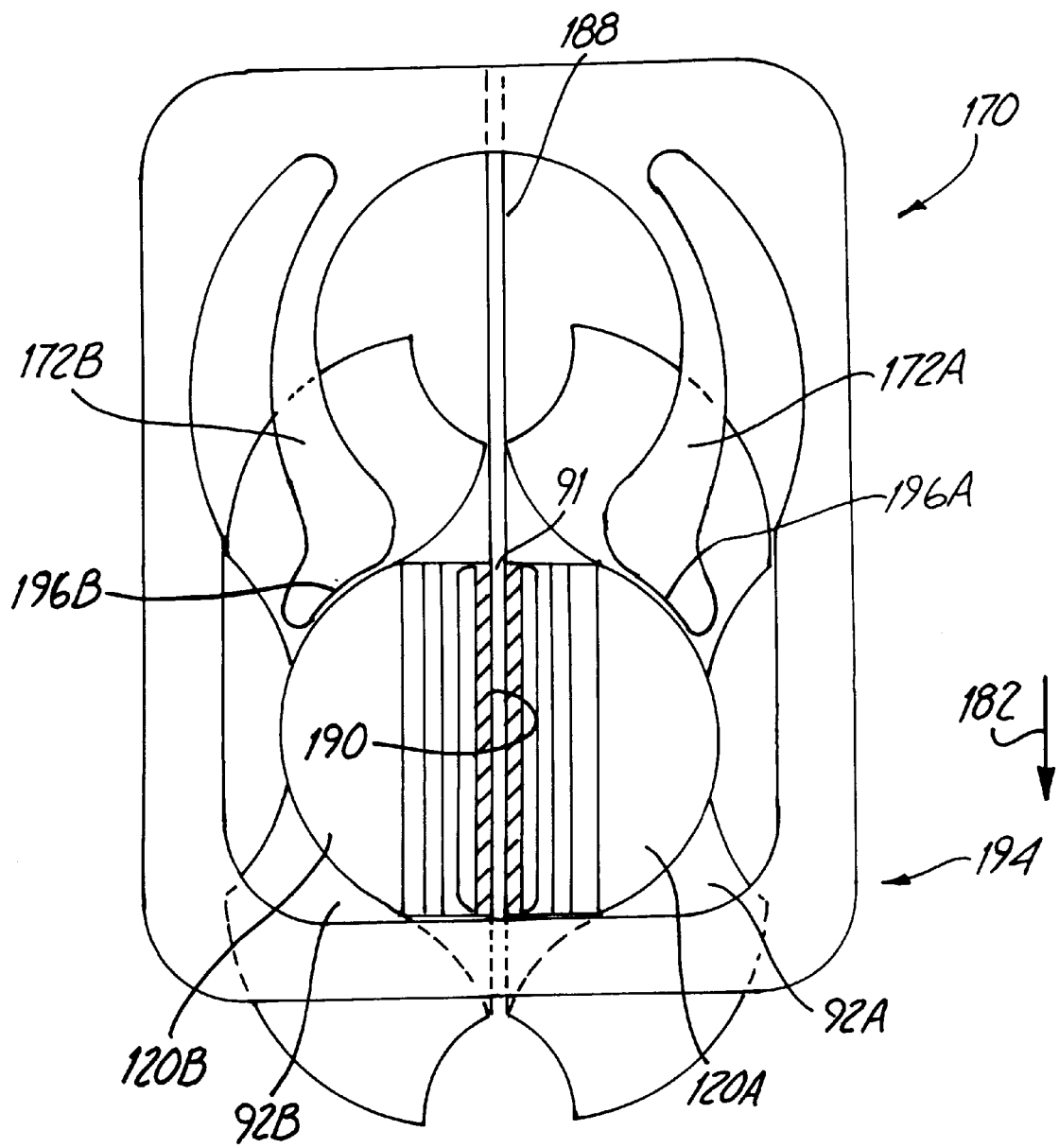
FIG. 21 is a sectional view of the holder of FIG. 17 in a disengaged position with a seventh embodiment of a locking collar.

Another embodiment of a locking collar 194 is illustrated in FIG. 21. The locking collar 194 is similar to the locking collar 170 and includes resilient members 172A and 172B to retain the proximal ends 120A and 120B in the engaged position. In this embodiment, diverging portions 196A and 196B are also provided on ends of the arcuate resilient members 172A and 172B, respectively. As illustrated, the diverging portions 196A and 196B partially surround the proximal ends 120A and 120B when the jaws 92A and 92B are free to pivot. The diverging portions 196A and 196B guide the proximal ends 120A and 120B together when the locking collar 194 is displaced in the direction indicated by arrow 182. If desired, the locking collars 170 and 194 can also be used on the holder 10 of FIG. 1.

Figure 22:
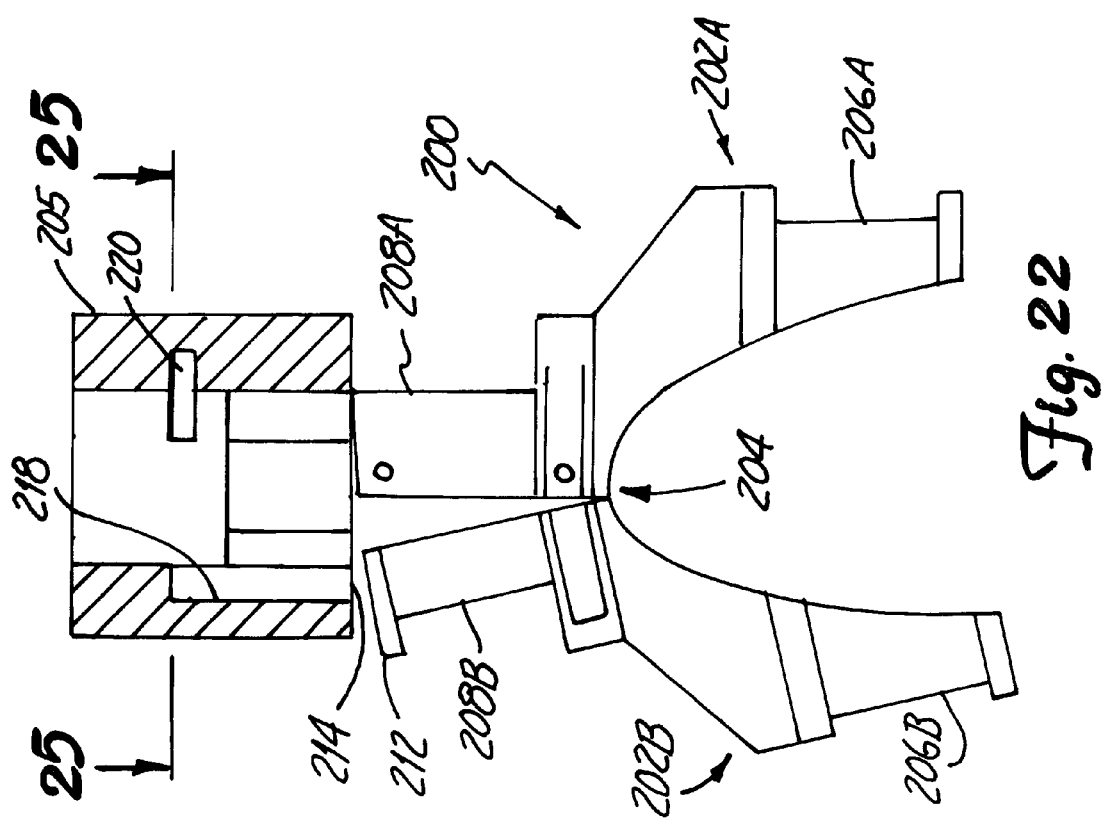
FIG. 22 is a front elevational view of a holder in a disengaged position with an eighth embodiment of a locking collar shown in section.

FIGS. 22, 23 and 24 illustrate another embodiment of a holder 200 with a locking collar 205 of the present invention. The holder 200 is commonly used by Carbomedics, Inc. of Austin, Tex. and includes a set of jaws 202A and 202B pivotally joined together with a hinge assembly 204. The jaws 202A and 202B are similar to each other. Distal ends 206A and 206B of the jaws 202A and 202B, respectively, are adapted to engage an inner circumferential surface of a heart valve, not shown. When proximal ends 208A and 208B of the jaws 202A and 202B are held fixed relative to each other, the distal ends 206A and 206B engage the heart valve. When the proximal ends 208A and 208B are free to move, the distal ends 206A and 206B release from the heart valve.

The locking collar 205 selectively inhibits pivotal movement of the proximal ends 208A and 208B. The locking collar 205 is movable between a first position illustrated in FIG. 22, in which the proximal ends 208A and 208B are free from the locking collar 205 to pivot, and a second position illustrated in FIG. 23, in which the locking collar 205 holds the proximal ends 208A and 208B such that the distal ends 206A and 206B are held in position to engage the heart valve.

Figure 25:
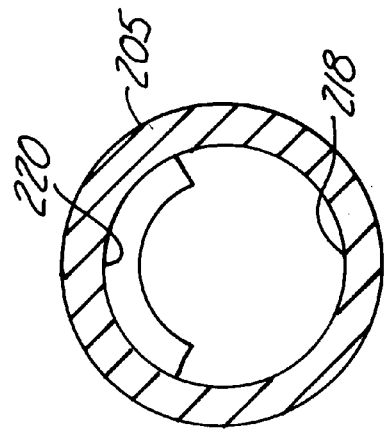
FIG. 25 is a sectional view of the eighth embodiment of the locking collar of the present invention taken along 25—25 in FIG. 22.

In this embodiment, the locking collar 205 selectively engages a flange 212 provided on the proximal end 208B. Referring to FIGS. 22 and 23, the locking collar 205 has an opening 214 of size to fit over the proximal ends 208A and 208B when joined together. In this position, the locking collar 205 holds the proximal ends 208A and 208B together, but sliding movement of the locking collar 205 in a direction indicated by double arrow 216 is possible in view that the flange 212 is aligned with a channel 218 that extends to the opening 214. However, when the locking collar 205 is rotated as illustrated in FIG. 24, the flange 212 is received in a recess 220. Coupling of the flange 212 in the recess 220 inhibits axial movement of the locking collar 205 on the holder 200. A sectional view of the locking collar 205 is illustrated in FIG. 25.

Figure 27:
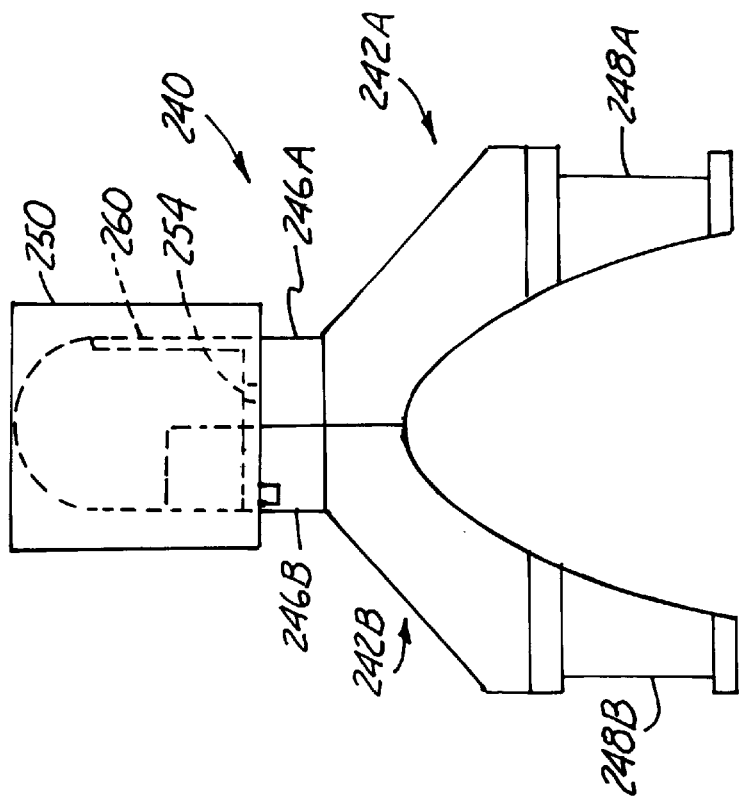
FIG. 27 is a front elevational view of the holder of FIG. 26 in an engaged position.
Figure 26:
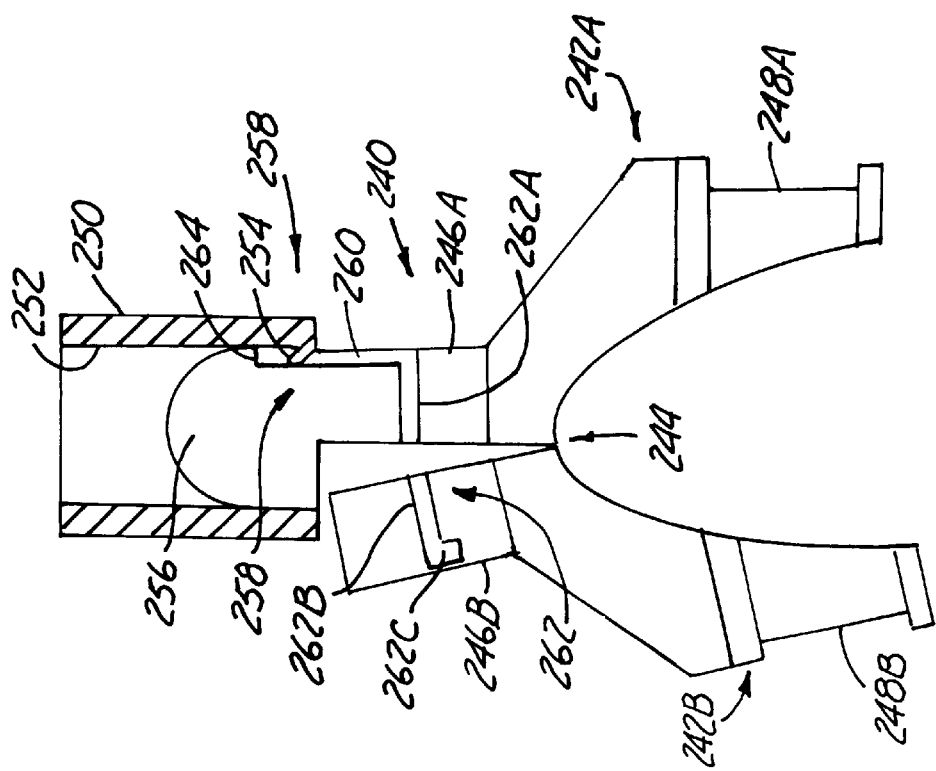
FIG. 26 is a front elevational view of a holder of the present invention in a disengaged position with a ninth embodiment of a locking collar shown in section.

Another embodiment of a holder 240 of the present invention is illustrated in FIGS. 26 and 27. The holder 240 includes a set of jaws 242A and 242B pivotally joined together with a hinge assembly 244. The jaws 242A and 242B are similar to each other. When proximal ends 246A and 246B of the jaws 242A and 242B, respectively, are held in a fixed position relative to each other, distal ends 248A and 248B engage an inner circumferential surface of a heart valve, not shown.

A locking collar 250 selectively inhibits pivotal movement of the proximal ends 246A and 246B. The locking collar 250 is movable between a first position illustrated in FIG. 26, in which the proximal ends 246A and 246B are free from the locking collar 250 to pivot, and a second position illustrated in FIG. 27, in which the locking collar 250 holds the proximal ends 246A and 246B fixed such that the distal ends 248A and 248B are held in position to engage a heart valve.

Figure 29:
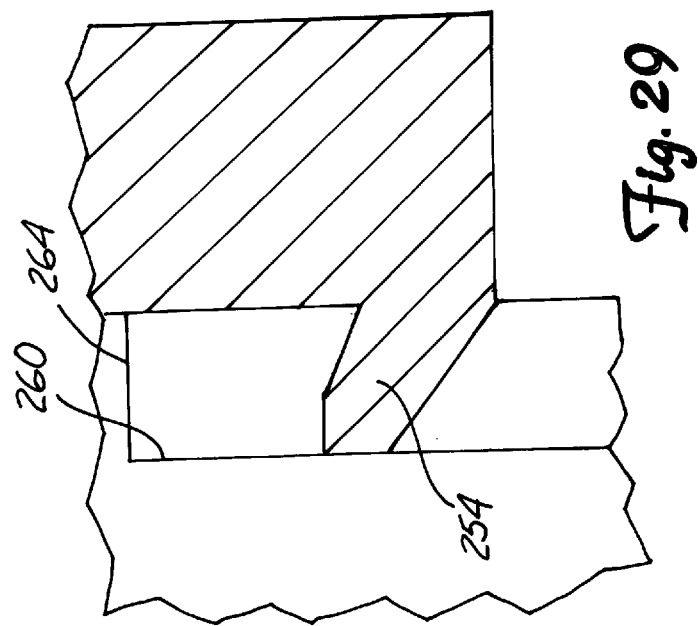
FIG. 29 is an enlarged portion of FIG. 26.
Figure 28:
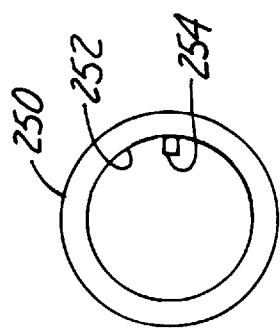
FIG. 28 is a top plan view of the ninth embodiment of the locking collar.

Referring also to FIGS. 28 and 29, the locking collar 250 includes an inner bore 252 of size and shape corresponding to the proximal ends 246A and 246B when joined together. A protrusion 254 extends into the inner bore 252. The protrusion 254 is received in a groove or channel 258 having an axial section 260 allowing axial movement of the locking collar 250 on the holder 240, and a radial section 262 having a first portion 262A formed in the proximal end 246A and a second portion formed in the proximal end 246B. When the locking collar 250 is moved toward the radial groove 262, and the proximal end 246B is positioned adjacent the proximal end 246A, the proximal ends 246A and 246B are held fixed relative to each other. Subsequent rotation of the locking collar 250 such that the protrusion enters either radial groove portion 262A or 262B inhibits axial movement of the locking collar 250. In the embodiment illustrated, an end groove portion 262C is provided in the proximal end 246B to indicate a locked position.

Although illustrated in FIGS. 22–24 where the groove 262 is provided on the proximal ends 246A and 246B, it should be understood that the groove 262 can be provided entirely on a stem such as stem 94, or a combination of the stem 94 and at least one of the proximal ends 120A and 120B.

Preferably, the protrusion 254 is slightly resilient in order that the protrusion 254 will bend. In this manner, the locking collar 250 can be slid over a stem 256 and the protrusion 254 will snap into the groove 260. As illustrated in FIG. 26, the groove 260 has an end surface 264 that inhibits removal of the locking collar 250 from the stem 256.

Each of the holders and locking collars of the present invention described above are easy to use and manufacture. The locking collars provide a secure and stable support for a prosthetic heart valve during manufacturing, shipping, and surgical implantation of the prosthetic heart valve in the patient.

The locking collars replace sutures commonly used to secure proximal ends of the holders together. The locking collars eliminate the cutting of sutures and eliminate potential damage to the heart valve and/or tissue which may result from cutting the sutures. Due to the elimination of the tying sutures, the locking collars of the present invention may be preferred in minimally invasive procedures. By using a locking collar of the present invention, surgeons can conveniently release the heart valve from the holder as well as reattach the holder to the heart valve if desired.

In addition, the locking collars eliminate assembler variability associated with hand tying of sutures, which are difficult to place around the proximal ends of the holder.

Although the present invention has been described with reference to preferred embodiments, workers skilled in the art will recognize that changes may be made in form and detail without departing from the spirit and scope of the invention.

What is claimed is:

1. A prosthetic heart valve holder for holding a prosthetic heart valve, the prosthetic heart valve holder comprising:
   a set of jaws, wherein each jaw includes a distal end adapted for coupling to the prosthetic heart valve and a proximal end;
   a hinge assembly pivotally coupling the jaws together between the distal and proximal ends and defining an axis of the holder wherein a jaw is positioned on each side of the axis and the axis extends from the proximal ends to the distal ends, the hinge assembly allowing movement of the jaws between an engaged position for grasping the prosthetic heart valve and a disengaged position in which the prosthetic heart valve is free from the distal ends; and
   a collar substantially rigid to maintain an aperture therethrough, the collar being movably attached to the jaws and slidable between a first position on the holder in which the proximal ends are free from the collar to pivot and a second position in which the proximal ends extend into the aperture and the collar holds the proximal ends of the jaws whereby the distal ends are held in position to engage the prosthetic heart valve.

2. The prosthetic heart valve holder of claim 1 wherein the collar is slidable on the jaws.

3. The prosthetic heart valve holder of claim 2 wherein the collar is slidable on the holder along a line non-parallel to the axis of the holder.

4. The prosthetic heart valve holder of claim 3 wherein the collar is slidable on the holder along a line substantially perpendicular to the axis of the holder.

5. The prosthetic heart valve holder of claim 4 wherein the collar includes at least one resilient member selectively engageable with one of the proximal ends of the set of jaws.

6. The prosthetic heart valve holder of claim 4 wherein the collar comprises a pair of resilient members selectively engageable with the proximal ends of the set of jaws.

7. The prosthetic heart valve holder of claim 2 wherein the collar is slidable substantially parallel to the axis of the holder.

8. The prosthetic heart valve holder of claim 7 wherein the collar is rotatable about the axis of the holder.

9. The prosthetic heart valve holder of claim 7 wherein the collar engages stop surfaces at the first position.

10. The prosthetic heart valve holder of claim 9 wherein a longitudinal length of a first portion of the collar is shorter than an adjacent portion of the collar to form a recessed stop surface.

11. The prosthetic heart valve holder of claim 2 wherein the collar includes a bore extending through the collar having a first opening on one end larger than a second opening on the other end.

12. The prosthetic heart valve holder of claim 2 wherein the collar includes a bore and a resilient member is secured to an inner surface of the collar about at least a portion of the bore.

13. The prosthetic heart valve holder of claim 1 wherein one of the jaws includes an extending portion, and wherein the locking collar is positioned on the extending portion in the first position.

14. The prosthetic heart valve holder of claim 1 and a stem having a proximal end and a distal end, and wherein the hinge assembly includes a first hinge formed between a first jaw of the set of jaws and the distal end of the stem, and a second hinge formed between a second jaw of the set of jaws and the distal end of the stem.

15. The prosthetic heart valve holder of claim 14 wherein the locking collar is slidable from the first position on the proximal end of the stem toward the distal end of the stem.

16. The prosthetic heart valve holder of claim 15 wherein the stem includes an extending flange to limit sliding movement of the locking collar.

17. The prosthetic heart valve holder of claim 16 and wherein the locking collar includes a recess selectively receiving the extending flange.

18. The prosthetic heart valve holder of claim 16 wherein a first portion of the locking collar contacts the extending flange in the first position and a second portion of the locking collar contacts the extending flange in the second position.

19. The prosthetic heart valve holder of claim 1 wherein one of the proximal ends includes an extending flange to limit sliding movement of the locking collar.

20. The prosthetic heart valve holder of claim 19 wherein the locking collar includes a recess selectively receiving the extending flange.

21. The prosthetic heart valve holder of claim 1 wherein the locking collar includes a bore and a protrusion extending into the bore and wherein one of the jaws includes a channel to receive the protrusion.

22. The prosthetic heart valve holder of claim 21 wherein the channel comprises a radial channel to allow the locking collar to rotate about an axis of the holder.

23. The prosthetic heart valve holder of claim 22 wherein the radial channel is disposed on one of the proximal ends.

24. The prosthetic heart valve holder of claim 22 and wherein the channel includes an axial portion allowing the locking collar to slide parallel to the axis of the holder from the first position to the second position.

25. A prosthetic heart valve holder for holding a prosthetic heart valve, the prosthetic heart valve holder comprising:

a set of jaws, wherein each jaw includes a distal end adapted for coupling to the prosthetic heart valve and a proximal end;

a hinge assembly pivotally coupling the jaws together between the distal and proximal ends and defining an axis of the holder wherein a jaw is positioned on each side of the axis and the axis extends from the proximal ends to the distal ends, the hinge assembly allowing movement of the jaws between an engaged position for grasping the prosthetic heart valve and a disengaged position in which the prosthetic heart valve is free from the distal ends; and a collar substantially rigid and formed from a single unitary piece to maintain an aperture therethrough, the collar being movably attached to the jaws and slidable between a first position in which the proximal ends are free from the collar to pivot and a second position in which the proximal ends extend into the aperture and the collar holds the proximal ends of the jaws whereby the distal ends are held in position to engage the prosthetic heart valve.

* * * * *